US012737885B2

(12) United States Patent
Oh et al.

(10) Patent No.: US 12,737,885 B2
(45) Date of Patent: Sep. 15, 2026

(54) MEDICAL IMAGE ANALYSIS ASSISTANCE SYSTEM AND METHOD FOR PROVIDING MEDICAL IMAGE ANALYSIS RESULTS

(71) Applicant: MONITOR CORPORATION CO., LTD., Seongnam-si (KR)

(72) Inventors: Dong Yul Oh, Seoul (KR); Jae Hyun Park, Seoul (KR)

(73) Assignee: MONITOR CORPORATION CO., LTD., Seongnam-si (KR)

( * ) Notice: Subject to any disclaimer, the term of this patent is extended or adjusted under 35 U.S.C. 154(b) by 111 days.

(21) Appl. No.: 18/832,914

(22) PCT Filed: Jan. 30, 2023

(86) PCT No.: PCT/KR2023/001351
§ 371 (c)(1),
(2) Date: Jul. 24, 2024

(87) PCT Pub. No.: WO2023/146368
PCT Pub. Date: Aug. 3, 2023

(65) Prior Publication Data

US 2025/0148590 A1 May 8, 2025

(30) Foreign Application Priority Data

Jan. 28, 2022 (KR) ........................ 10-2022-0013399

(51) Int. Cl.
*G06T 7/00* (2017.01)
*G06T 7/73* (2017.01)
(Continued)

(52) U.S. Cl.
CPC .............. *G06T 7/0012* (2013.01); *G06T 7/73* (2017.01); *G06T 11/26* (2026.01); *G16H 30/20* (2018.01);
(Continued)

(58) Field of Classification Search
CPC . G06T 2207/30061; G06T 7/73; G06T 11/26; G06T 2207/10081; G06T 2207/10088; G16H 30/20
See application file for complete search history.

(56) References Cited

U.S. PATENT DOCUMENTS

2014/0191753 A1 7/2014 Oh et al.
2018/0242817 A1* 8/2018 Imaizumi ......... A61B 1/000094
(Continued)

FOREIGN PATENT DOCUMENTS

GB 2639686 A * 1/2023 ............... A61B 1/00
JP 2006055235 A * 3/2006
(Continued)

OTHER PUBLICATIONS

International Search Report for PCT/KR2023/001351 mailed May 1, 2023 from Korean Intellectual Property Office.
(Continued)

*Primary Examiner* — Temesghen Ghebretinsae
(74) *Attorney, Agent, or Firm* — Revolution IP, PLLC

(57) ABSTRACT

The medical image analysis assistance system according to the embodiment of the present invention includes a lesion reading unit that estimates a presence of lesion from a plurality of medical images by reading medical image information including the plurality of medical images captured of a patient's body, and detects a position and information of the estimated lesion, and a readout information generation unit that generates readout information displaying markings related to the lesion on a scout image including at least one of the medical images in which the lesion is present and the medical images generated based on the plurality of medical images to represent the lesion, wherein the markings are displayed on the scout image corresponding to the position of the lesion and are displayed in different
(Continued)

diagrams according to a type of the lesion, a medical image analysis support system.

11 Claims, 12 Drawing Sheets

(51) Int. Cl.

*G06T 11/20* (2026.01)
*G06T 11/26* (2026.01)
*G16H 30/20* (2018.01)

(52) U.S. Cl.

CPC ............... *G06T 2207/10081* (2013.01); *G06T 2207/10088* (2013.01); *G06T 2207/30061* (2013.01); *G06T 2207/30096* (2013.01); *G06T 2207/30204* (2013.01); *G06T 2210/41* (2013.01)

(56) References Cited

U.S. PATENT DOCUMENTS

| | | | | |
|---|---|---|---|---|
| 2018/0333589 | A1 | 11/2018 | Kim | |
| 2019/0272640 | A1* | 9/2019 | Sugahara | G06V 10/776 |
| 2020/0193236 | A1* | 6/2020 | Oosake | G06V 10/454 |
| 2021/0151171 | A1 | 5/2021 | Lee et al. | |
| 2021/0407637 | A1 | 12/2021 | Park et al. | |
| 2023/0053318 | A1* | 2/2023 | Wicklein | G06T 7/187 |

FOREIGN PATENT DOCUMENTS

| | | | |
|---|---|---|---|
| JP | 2008-006091 | A | 1/2008 |
| JP | 2014-033948 | A | 2/2014 |
| JP | 2020-203077 | A | 12/2020 |
| KR | 10-0996050 | B1 | 11/2010 |
| KR | 10-1463420 | B1 | 11/2014 |
| KR | 10-1580075 | B1 | 1/2016 |
| KR | 10-2132566 | B1 | 7/2020 |
| KR | 10-2270934 | B1 | 6/2021 |
| KR | 10-2021-0158682 | A | 12/2021 |
| WO | 2021-112205 | A1 | 6/2021 |

OTHER PUBLICATIONS

Office Action of Japanese Patent Application No. 2024-545008 mailed Apr. 28, 2025.

Notice of Allowance of Japanese Patent Application No. 2024-545008 mailed Oct. 28, 2025.

* cited by examiner

MEDICAL IMAGE ANALYSIS ASSISTANCE SYSTEM AND METHOD FOR PROVIDING MEDICAL IMAGE ANALYSIS RESULTS

TECHNICAL FIELD

The present invention relates to a medical image analysis assistance system and a method for providing medical image analysis results, and in more detail, a medical image analysis assistance system for assisting in the diagnosis of lesion in a medical image and a method for providing medical image analysis results using the same.

BACKGROUND ART

Many hospitals use a medical imaging information system (PACS, Picture Archiving Communications System) that is linked to equipment that captures medical images such as X-rays, CT, and MRI images.

The medical imaging information system stores the captured medical images in a digital form and transmits them to the clinician's pc, so that the clinician checks the medical images from the pc and diagnoses the patient's lesions.

In particular, the CT, MRI images are composed of 300 continuous tomographic images, and the clinician checks the 300 images to check the lesions without any error and has the burden of accurate diagnosis.

DISCLOSURE

Technical Problem

The problem to be solved by the present invention is to provide a medical image analysis assistance system and a method for providing medical image analysis results that can more conveniently and accurately diagnose lesions by the user.

The technical problems of the present invention are not limited to the above-mentioned technical problems, and other technical problems not mentioned may be clearly understood by those skilled in the art from the following description.

Technical Solution

The medical image analysis assistance system according to the embodiment of the present invention to solve the above problem includes a lesion readout unit that reads medical image information including a plurality of medical images captured by a patient's body, estimates the presence of a lesion in the plurality of medical images, and detects the estimated position and information of the lesion, and a readout information generation unit that generates readout information that displays markings on the lesion on a scout image that includes at least one of the medical images where the lesion exists and the medical images generated based on the plurality of medical images so that the lesion is expressed, wherein the markings are displayed to correspond to the position of the lesion in the scout image and are displayed in different diagrams according to the type of the lesion.

The medical image analysis assistance system according to the embodiment of the present invention to solve the above problem includes a lesion readout unit that reads medical image information including a plurality of medical images captured by a patient's body, estimates the presence of a lesion in the plurality of medical image images, detects the estimated position and information of the lesion, and generates readout information that displays markings on the lesion on a scout image that includes at least one of the medical images where the lesion exists and the medical images generated based on the plurality of medical images so that the lesion is expressed, wherein the markings are displayed to correspond to the position of the lesion in the scout image and are displayed in different diagrams according to the type of the lesion.

Other details of the present invention are included in the detailed description and drawings.

Advantageous Effects

According to the embodiments of the present invention, at least the following effects are possible.

The user can diagnose the lesion more conveniently and accurately.

The effects according to the present invention are not limited by the above-exemplified contents, and various effects are included in the present specification.

DESCRIPTION OF DRAWINGS

FIG. 12 is a diagram for explaining a method of utilizing a scout image according to the present invention.

MODE FOR INVENTION

Figure 1:
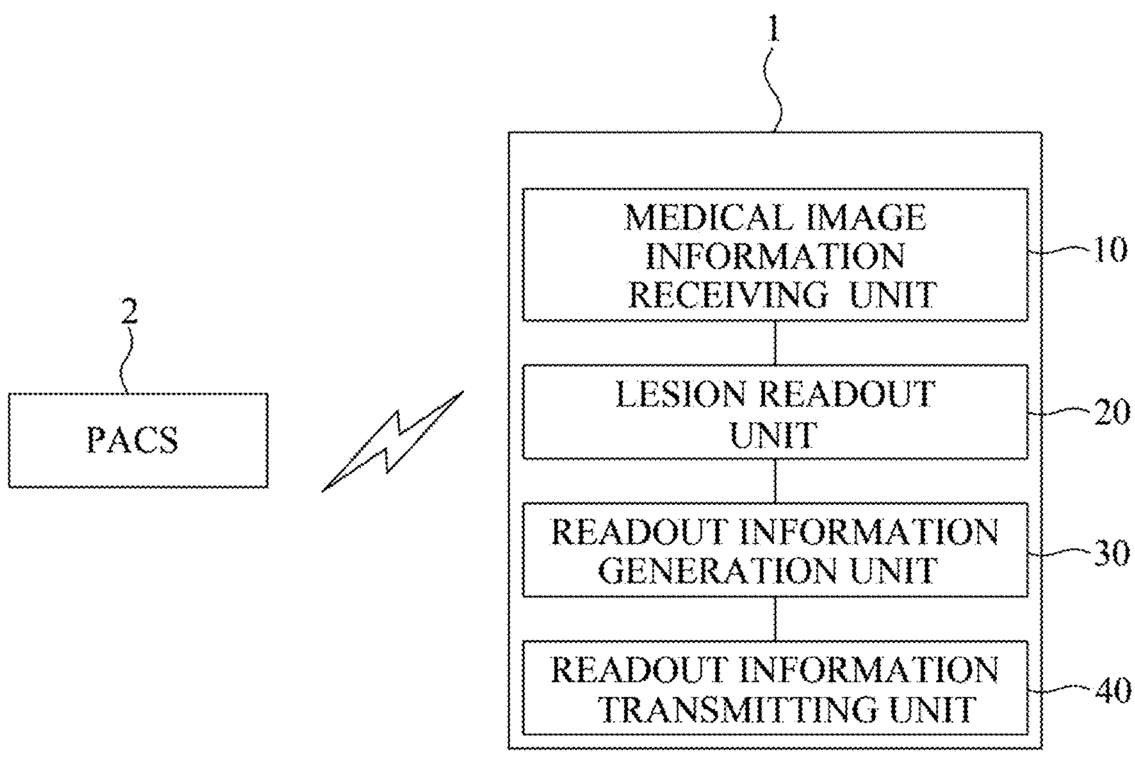
FIG. 1 is a diagram schematically illustrating a system in which a medical image analysis assistant system according to an embodiment of the present invention is used.

The advantages and features of the present invention, and the methods of achieving them, will become apparent by reference to the embodiments described in detail below together with the accompanying drawings. However, the present invention is not limited to the embodiments disclosed below, but may be implemented in various forms different from each other, and the present embodiments are provided so that the disclosure of the present invention is complete, and the scope of the invention is completely known to those skilled in the art to which the present invention pertains, and the present invention is defined only by the scope of the claims.

In addition, the embodiments described herein will be described with reference to cross-sectional views and/or schematic views, which are ideal examples of the present invention. Therefore, the shape of the exemplary diagram may be modified by manufacturing technology and/or tolerances. In addition, in each drawing illustrated in the present invention, each component may be slightly enlarged or reduced in consideration of convenience of explanation. Throughout the specification, the same reference numerals refer to the same components.

Hereinafter, the present invention will be described with reference to the drawings to explain the medical image analysis assistance system and the method of providing the medical image analysis result using the same according to the embodiment of the present invention.

Figure 2:
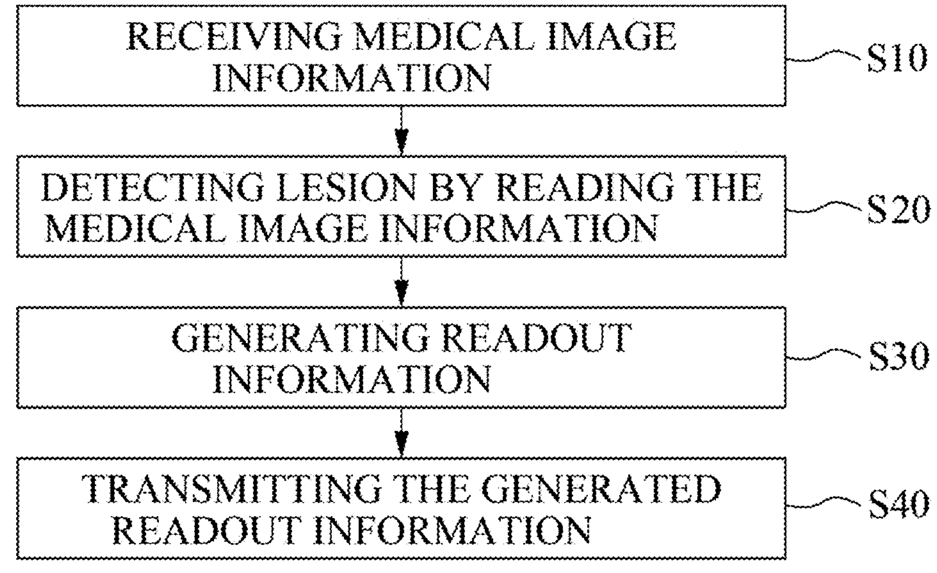
FIG. 2 is a flowchart for explaining a method of providing a medical image analysis result according to an embodiment of the present invention.

FIG. 1 is a diagram schematically illustrating a system in which a medical image analysis assistant system according to an embodiment of the present invention is used, and FIG. 2 is a flowchart for explaining a method of providing a medical image analysis result according to an embodiment of the present invention.

Referring to FIG. 1, the medical image analysis assistance system 1 according to an embodiment of the present invention is communicatively connected to the Picture Archiving Communications System (PACS) 2. PACS is a medical video information system that is currently widely used in hospitals.

In this embodiment, the medical image analysis assistance system 1 is connected to the medical image information system, and the medical image analysis assistance system 1 according to an embodiment of the present invention may be connected to other medical image information systems other than the PACS 2 so as to communicate.

The medical image analysis assistant system 1 may exist at a remote location outside the hospital, and in this case, it may be communicatively connected to the PACS 2 through a wired/wireless telecommunication network. For example, the medical image analysis assistance system 1 and PACS 2 may be connected through a wide area network such as the Internet.

Alternatively, the medical image analysis assistance system 1 may be located in the hospital that operates the PACS 2. In this case, the medical image analysis assistant system 1 may be communicatively connected to the PACS 2 through a wired/wireless communication network within the hospital.

In addition, the medical image analysis assistance system 1 may be communicatively connected to an input device and a terminal having a screen. The terminal may be an electronic device such as a desktop, a laptop, a tablet, a smartphone, etc.

The medical image analysis assistant system 1 may be connected to a terminal in a remote location and to communicate with the terminal through a wired/wireless remote communication network. For example, the medical image analysis assistant system 1 may be connected to a terminal in a cloud manner to provide a service.

Alternatively, the medical image analysis assistance system 1 may be provided as software installed in the terminal.

Alternatively, some components of the medical image analysis assistant system 1 may be provided as software installed in the terminal, and other components may be provided in remote locations and connected to the terminal to communicate with the terminal through a wired/wireless telecommunication network.

Referring to FIG. 1, the medical image analysis assistant system 1 according to an embodiment of the present invention may include a medical image information receiving unit 10, a lesion readout unit 20, a readout information generation unit 30, and a readout information transmitting unit 40.

Further, referring to FIG. 2, the method for providing the medical image analysis result according to an embodiment of the present invention may include receiving medical image information (s10), detecting lesion by reading the medical image information (s20), generating readout information (s30), and transmitting the generated readout information (s40).

In the step of receiving medical image information (s10), the medical image information receiving unit 11 receives the medical image information generated by the medical imaging apparatus stored in the PACS 2 or associated with the PACS 2 from the PACS 2. The medical image information may be data in the form of Digital Imaging Communication in Medicine (DICOM), which is standardized medical image information currently commonly used. In this embodiment, the description will be made based on the medical image information including the medical image captured using a medical imaging apparatus such as Computer Tomography (CT), Magnetic Resonance Imaging (MRI), etc., in which a plurality of medical images captured continuously by the body section of the patient are configured as one set.

In the step of detecting lesion by reading the medical image information (s20), the lesion readout unit 20 estimates the presence of the lesion by reading the plurality of medical images included in the medical image information acquired by the medical image information receiving unit 10, and detects location information in the image of the estimated lesion. The lesion readout unit 20 may be configured to read the medical image based on artificial intelligence (AI), and detect the lesion estimated to be present in the image.

For example, the lesion readout unit 20 may detect nodules in the lung by using Computer Aided Detection (CAD) algorithm on the image of the lung portion from the plurality of medical images (e.g., CT images) included in the medical image information. The lesion readout unit 20 may read the location, size, volume, type, hounsfield, category, etc of the detected nodules.

The type may be classified into non-solid nodules, part-solid nodules, solid nodules, calcification nodules, or unknown. The category may be classified into 1, 2, 3, 4A, and 4B according to Lung-RADs. The category may be classified based on the size, volume, type, and hounsfield information of the detected nodules.

Figure 3:
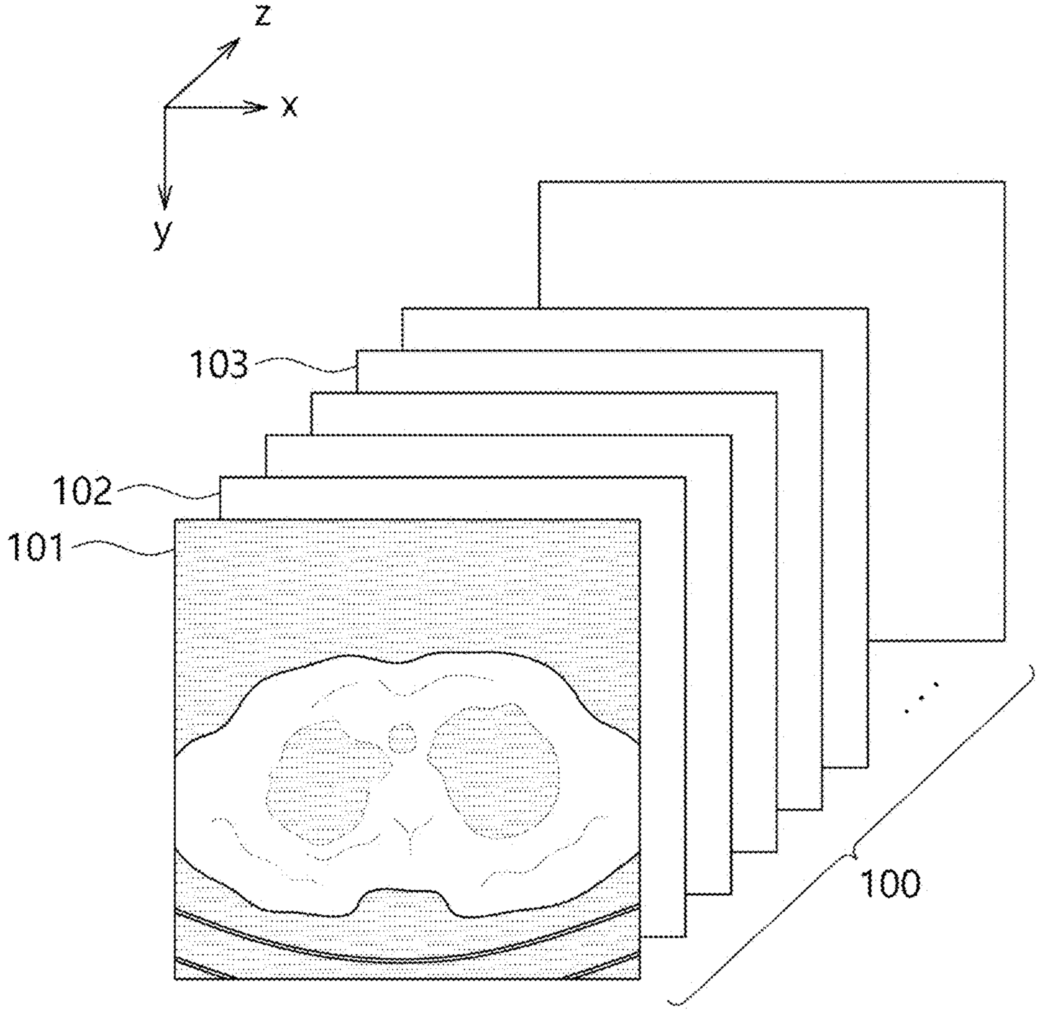
FIG. 3 is a diagram schematically illustrating medical image information according to an embodiment including a plurality of medical images.

FIG. 3 is a diagram schematically illustrating medical image information according to an embodiment including a plurality of medical images.

Referring to FIG. 3, the medical image information 100 may include a plurality of medical images 101. For example, the medical image information 100 may include a 360 axial slice image 101.

The lesion readout unit 20 performs reading on each medical images 101, estimates the presence of a lesion in each medical image 101, and detects the location and information of the estimated lesion.

For convenience of explanation, the description will be given below based on the case that herein the lesion readout unit 20 estimates the presence of a lesion in two medical images 102 and 103.

Figure 4:
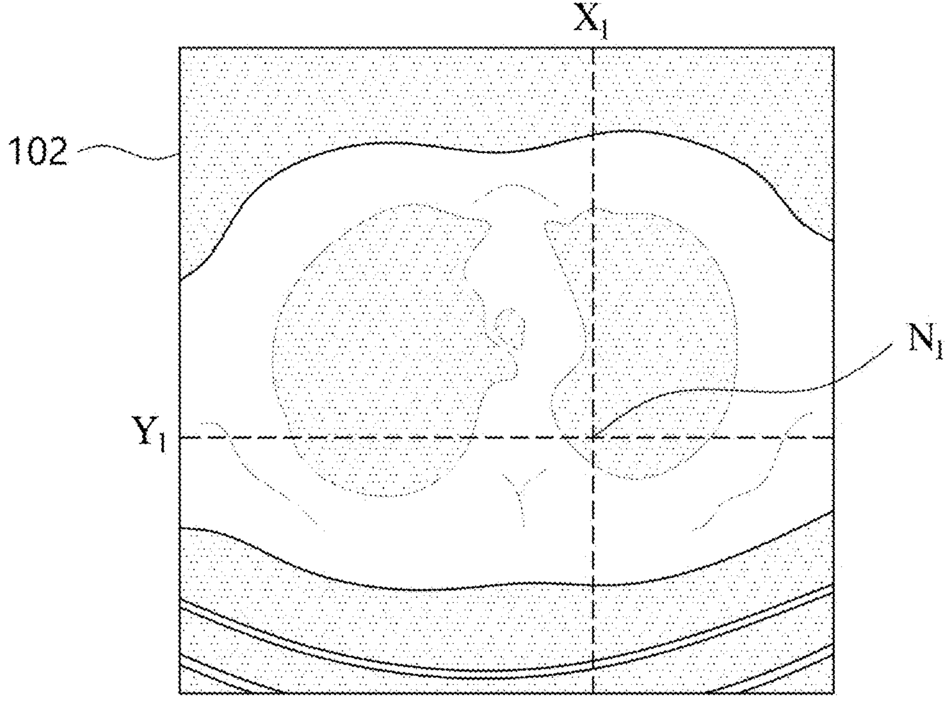
FIG. 4 is a diagram illustrating a first medical image in which a first lesion is detected.
Figure 5:
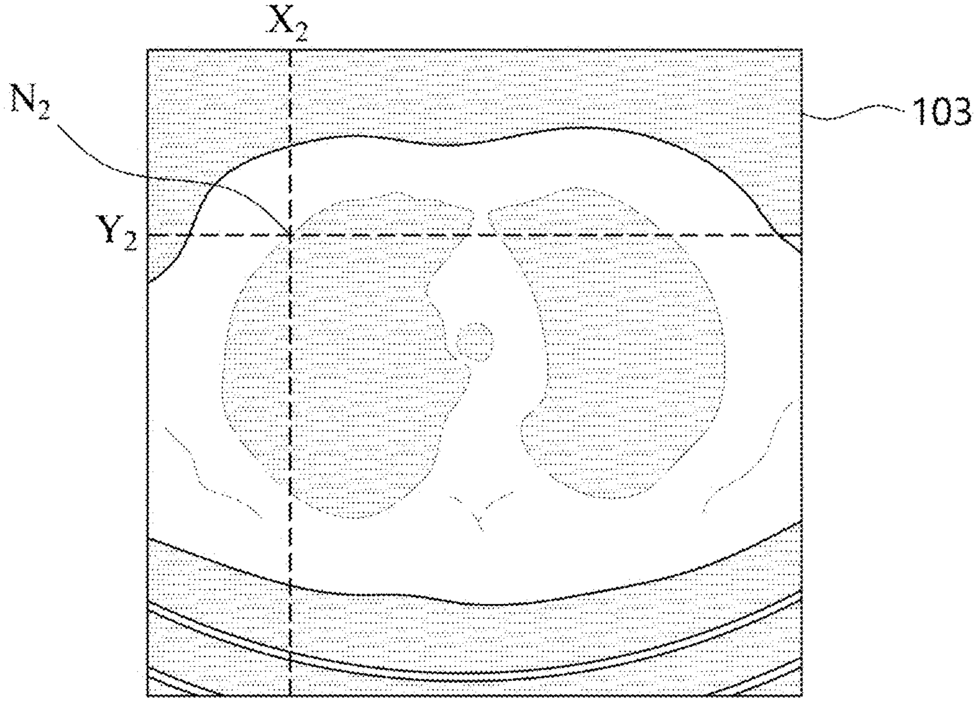
FIG. 5 is a diagram illustrating a second medical image in which a second lesion is detected.

FIG. 4 is a diagram showing a first medical image image in which detects a first lesion, and FIG. 5 is a second medical image in whichs a second lesion.

Referring to FIG. 3, each pixel of each medical images 101 may be expressed as a three-axis coordinate (x, y, z).

Referring to FIG. 4, the first lesion N1 found in the first medical image image 102 is located on the coordinates of (x1, y1, z1). The z-axis coordinates of all pixels of the first medical image image 102 are the same as Z1.

Referring to FIG. 5, the second lesion N2 found in the second medical image image 103 is located on the coordinates of (x2, y2, z2). The z-axis coordinates of all pixels of the second medical image image 103 are the same as Z2.

The lesion readout unit 20 may read not only the location information of the first lesion N1 and the second lesion N2, but also the size, volume, type, hounsfield, and category of the first lesion N1 and the second lesion N2, as described above.

In the step of generating the readout information (s30), the readout information generation unit 30 generates read information using information on lesions detected by the lesion readout unit 20.

The readout information generation unit 30 may generate a scout image as reading information.

Figure 6:
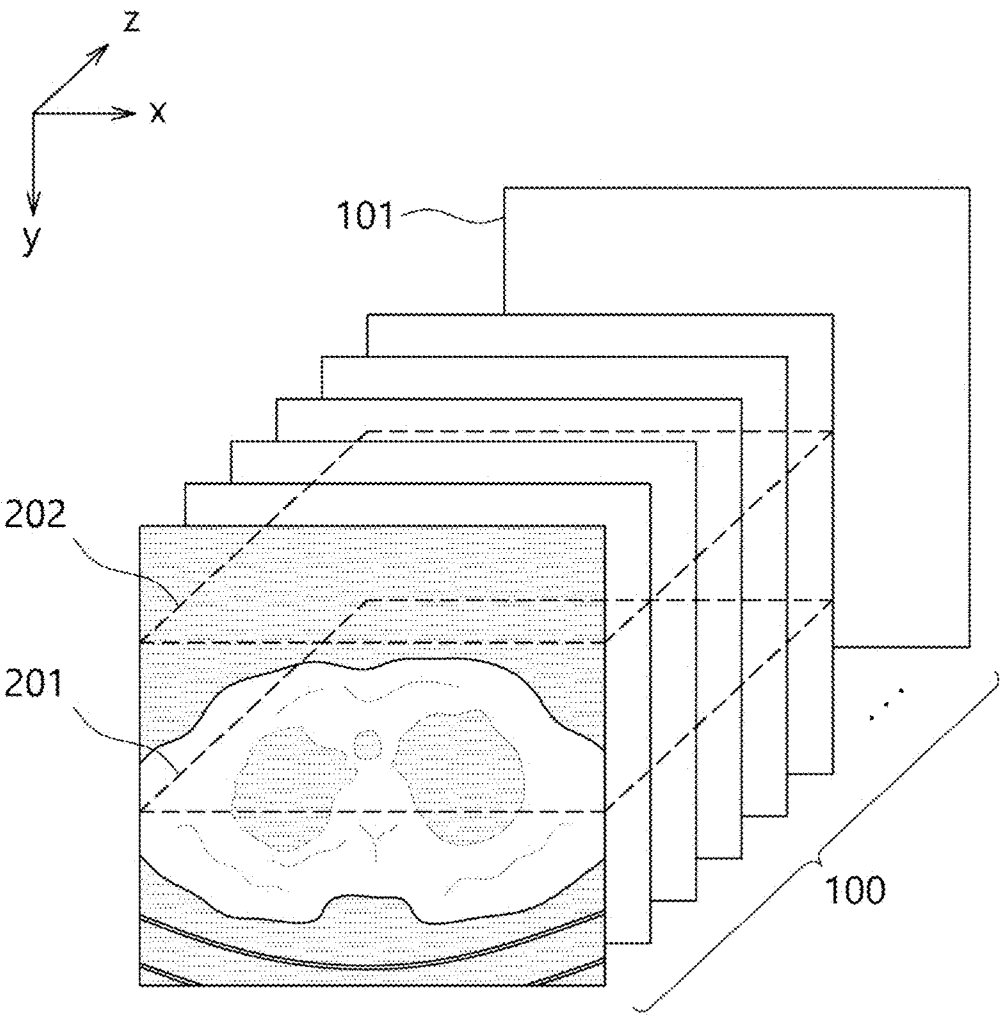
FIG. 6 is a diagram for explaining a method of generating a scout image.
Figure 7:
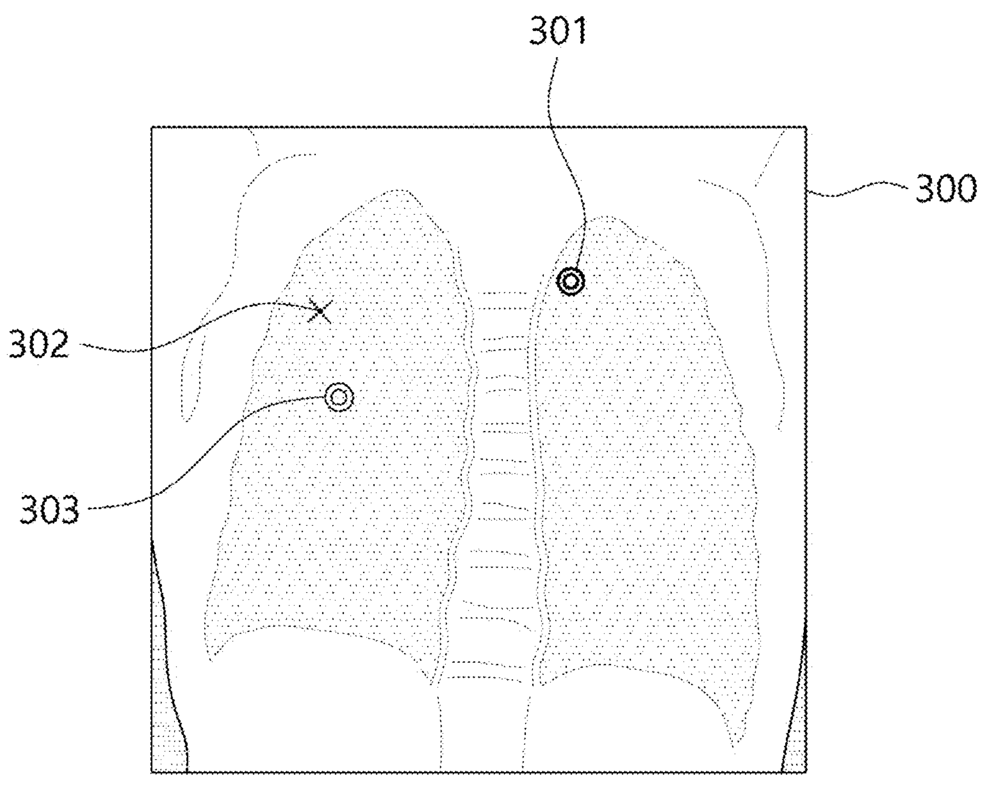
FIG. 7 is a diagram illustrating a first scout image in which markings are displayed on a first lesion.
Figure 8:
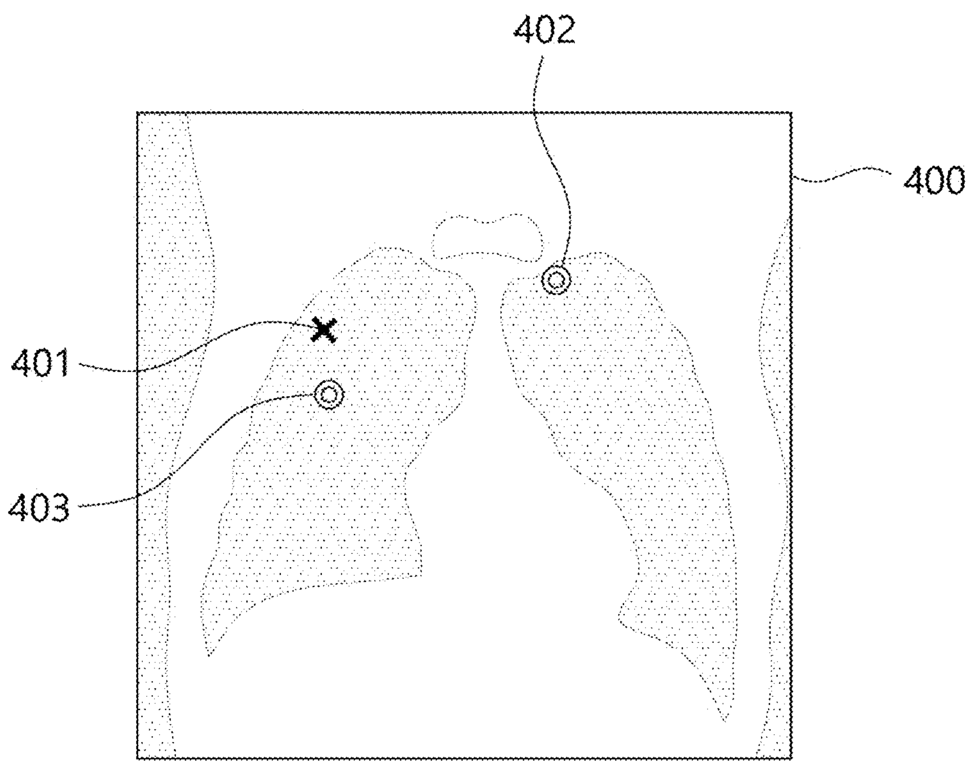
FIG. 8 is a diagram illustrating a second scout image in which markings are displayed on a second lesion.

FIG. 6 is a diagram for explaining a method of generating a scout image, FIG. 7 is a diagram showing a first scout image in which marking is displayed on a first lesion, and FIG. 8 is a diagram showing a second scout image in which marking is displayed on a second lesion.

Referring to FIGS. 3 to 6, the first lesion N1 is located on the first Y-plane 201, and the second lesion N2 is located on the second Y-plane 202.

The readout information generation unit 30 may generate a coronal image represented by the first lesion N1 as a scout image represented by the first lesion N1. In this case, the readout information generation unit 30 may combine an image of pixels whose Y-axis coordinate value is the same as the Y-axis coordinate (Y-1) of the first lesion N1 in the plurality of medical images 101 to generate the first scout image 300 with the coronal image represented by the first lesion N1, as shown in FIG. 7.

In addition, the readout information generation unit 30 may generate a coronal image in which the second lesion N2 is expressed as a scout image. In this case, the readout information generation unit 30 may combine an image of pixels whose Y-axis coordinate value is the same as the Y-axis coordinate (Y-2) of the second lesion (N2) in the plurality of medical images (101), and generate the second scout image (400) by expressing the second lesion (N2) as shown in FIG. 1.

When the readout information generation unit 30 generates a sagittal image as a scout image, the readout information generation unit 30 may generate a sagittal image as a scout image by combining images of pixels having the same x-axis coordinate value as the X-axis coordinate of the corresponding lesion in the plurality of medical images 101.

Alternatively, when the readout information generation unit 30 uses the axial image as the scout image, the readout information generation unit 30 may not generate the scout image newly, and may use the medical images 101 as the scout image.

Meanwhile, referring to FIG. 7, the readout information generation unit 30 may generate readout information by displaying a first marking 301 for a first lesion n1 on the first scout image 300. Referring to FIG. 8, the readout information generating unit 30 may generate readout information by displaying a second marking 401 for a second lesion N2 on the second scout image 400.

As shown in FIGS. 7 and 8, markings 301 and 401 may be displayed to correspond to the location of the lesion in the scout image. For example, the markings 301 and 401 may be displayed to overlap with the location of the lesion in the scout image, to indicate the location of the lesion, or to surround at least a portion of the lesion.

The readout information generation unit 30 may display the markings 301 and 401 in different diagrams according to the type of the lesion, so that the user who checks the scout image may easily recognize the type of the lesion on which the marking is displayed only by checking the marking.

For example, when the lesion is a nodule, the nodule may be classified into types such as non-solid nodule, part-solid nodule, solid nodule, calcification nodule, or unknown, etc.

For example, the readout information generation unit 30 may display a marking for a non-solid nodule as a dotted diagram, a marking for a part-solid nodule as a solid diagram, a marking for a solid nodule as a double solid diagram, a marking for a calcification nodule as an internally filled diagram, and an unknown as an X-shaped diagram.

Referring to 9, the marking may be displayed as a diagram having a difference in the thickness of the line, the color of the line, etc., as well as the type of line.

Meanwhile, the readout information generation unit 30 may display the size of the diagram to be correlated with the size of the lesion. In other words, the larger the size of the lesion, the larger the marking, the larger the marking, the readout information generation unit 30 can be displayed. Therefore, a user who checks the scout image can easily recognize the absolute size or relative size of the lesion on which the marking is displayed only by checking the marking.

Meanwhile, as illustrated in FIGS. 7 and 8, the readout information generation unit 30 may display markings 302, 303, 402, and 403 of lesions located on different Y-plane on each scout image 300 and 400. In this case, markings 301 and 401 for lesions located on the same plane as the scout images 300 and 400 may be displayed to be distinguished from markings 302, 303, 402 and 403 for lesions located on different planes from the scout images 300 and 400. For example, markings 301 and 401 for lesions located on the same plane as scout images 300 and 400 may be more thicker, or different colors than markings 302, 303, 402, and 403 for lesions located on different planes than scout images 300 and 400.

Figure 9:
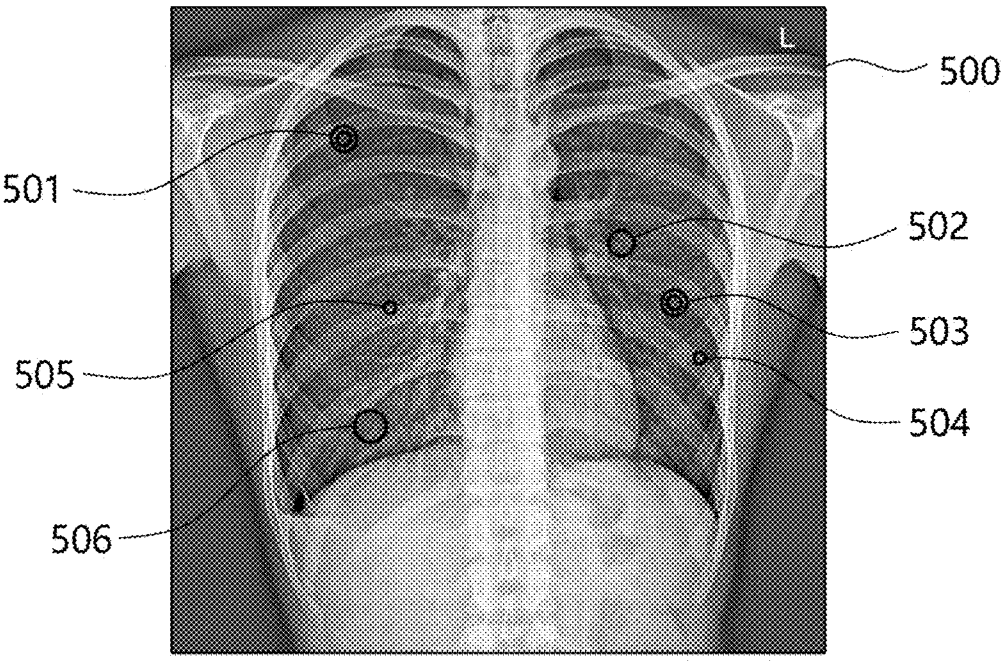
FIG. 9 is a diagram illustrating an example of a scout image in which markings are displayed on a plurality of lesions, respectively.

FIG. 9 is a diagram illustrating an example of a scout image in which markings are displayed on each of a plurality of lesions.

Referring to FIG. 9, the readout information generation unit 30 may generate readout information displayed on a single scout image 500 by markings 501, 502, 503, 504, 505, and 506 for all lesions read out in the medical image information 100.

In step S40 of transmitting the generated readout information, the readout information transmitting unit 40 may transmit the generated readout information to the PACS 2 through step S30.

The readout information transmitted by the readout information transmitting unit 40 to the PACS 2 may be dicom-type data. Therefore, the hospital who received the readout information may check the scout image and the marking included in the readout information using the PACS 2.

As shown in FIGS. 7 and 8, the readout information may include at least one of scout images generated for each lesion and marked with marking, and one scout image displayed with marking for all lesions.

Figure 10:
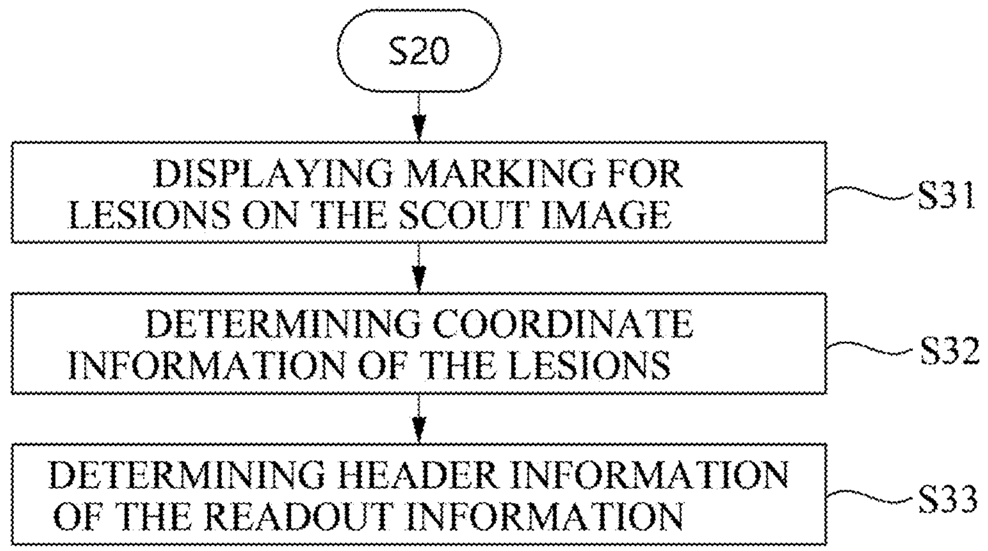
FIG. 10 is a flowchart for explaining the step s30 of FIG. 2.

FIG. 10 is a flowchart for describing the step S30 of FIG. 2.

Referring to FIG. 10, the step of generating the readout information S30 may include the step of displaying marking for lesions on the scout image S31, the step of determining coordinate information of the lesions S32, and the step of determining header information of the readout information S33.

The step of displaying marking for lesions on the scout image S31 has been described above with reference to FIGS. 6 to 8, and thus additional descriptions thereof will be omitted.

The method for providing the medical image analysis assistance system and the medical image analysis result according to an embodiment of the present invention may further include the steps S32 and S33 according to the embodiment.

In the step of determining the coordinate information of the lesions, the readout information generating unit 30 calculates the coordinate information of the detected lesions.

Figure 11:
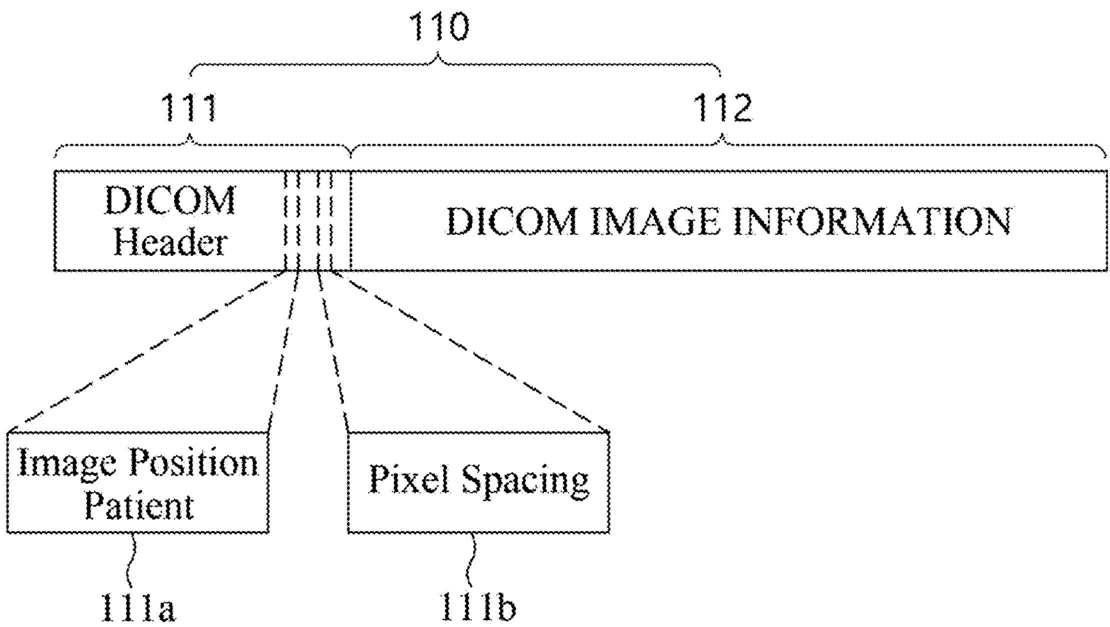
FIG. 11 is a diagram schematically illustrating a configuration of dicom-type data.

FIG. 11 is a schematic diagram illustrating the configuration of dicom-type data.

The plurality of slice image information 110 constituting the dicom-type medical image information 100 includes dicom header information 111 and dicom image information 112. The dicom image information 112 includes information for configuring the above-described slice image 101.

The dicom header information 111 records various types of information on the dicom image information 112. For example, the DICOM header information 111 includes patient information, photographing device information, image position patient information 111*a*, and pixel spacing information 111*b*.

In step S32, the readout information generating unit 30 calculates the coordinate information of the detected lesions using the image position patient information 111*a* and the pixel spacing information 111*b*.

Referring to FIG. 4, the step S32 will be described in more detail.

The readout information generating unit 30 may check the image position patient information 111*a* and the pixel spacing information 111*b* from the DICOM header information 111 of the first medical image image 102 detected by the first lesion N1.

X1 means the number of pixels from the upper left corner point of the first medical image image 102 to the pixel detected by the first lesion N1 in the x-direction (see FIG. 3).

Y1 means the number of pixels from the upper left corner point of the first medical image image 102 to the pixel detected by the first lesion N1 in the y-direction (see FIG. 3).

The pixel spacing information 111*b* means information on the interval between pixels.

The image position patient information 111*a* includes information on the reference coordinates of the first medical image image image 102. Referring to FIG. 3, the medical image information 100 includes a plurality of the axial medical image image 101, and the image position patient information 111*a* of each of the axial medical image 101 has the same coordinates as the x and the y, and only different z.

The coordinate indicated by the image position patient information 111*a* may be the upper left corner point of the medical image 101 or the center point of the medical image 101.

The readout information generation unit 30 may calculate the coordinate information of the first lesion N1 using the following formula.

$$Xreal=u+Sx\cdot X1$$

$$Yreal=v+Sy\cdot Y1$$

The coordinate indicated by the image position placement information 111*a* is (u, v, w), Sx is an X-axis pixel spacing among the pixel spacing information 111*b*, and Sy is a Y-axis pixel spacing among the pixel spacing information 111*b*.

Xreal means the actual x-coordinate of the first lesion N1, and Yreal means the actual y coordinate of the first lesion N1.

The actual z-coordinate of the first lesion N1 is the same as w.

The reading information generation unit 30 may generate (Xreal, Yreal, w) as the coordinate information of the first lesion N1.

In the step of determining the header information of the readout information (S33), the readout information generation unit 30 determines the image position placement information as the coordinate information of the lesion calculated in the step of S32 from the DICOM header information of the scout image.

That is, the readout information generation unit 30 may determine to indicate the image position placement information (Xreal, Yreal, w) from the DICOM header information of the readout information including the scout image of the first lesion N1.

Alternatively, the readout information generation unit 30 may determine to indicate the image position placement information (u, Yreal, w) from the DICOM header information of the readout information including the scout image of the first lesion N1.

In the step of transmitting the generated readout information (S40), the readout information transmitting unit 40 may transmit the readout information generated through the steps 31 to 32 to the PACS 2.

Figure 12:
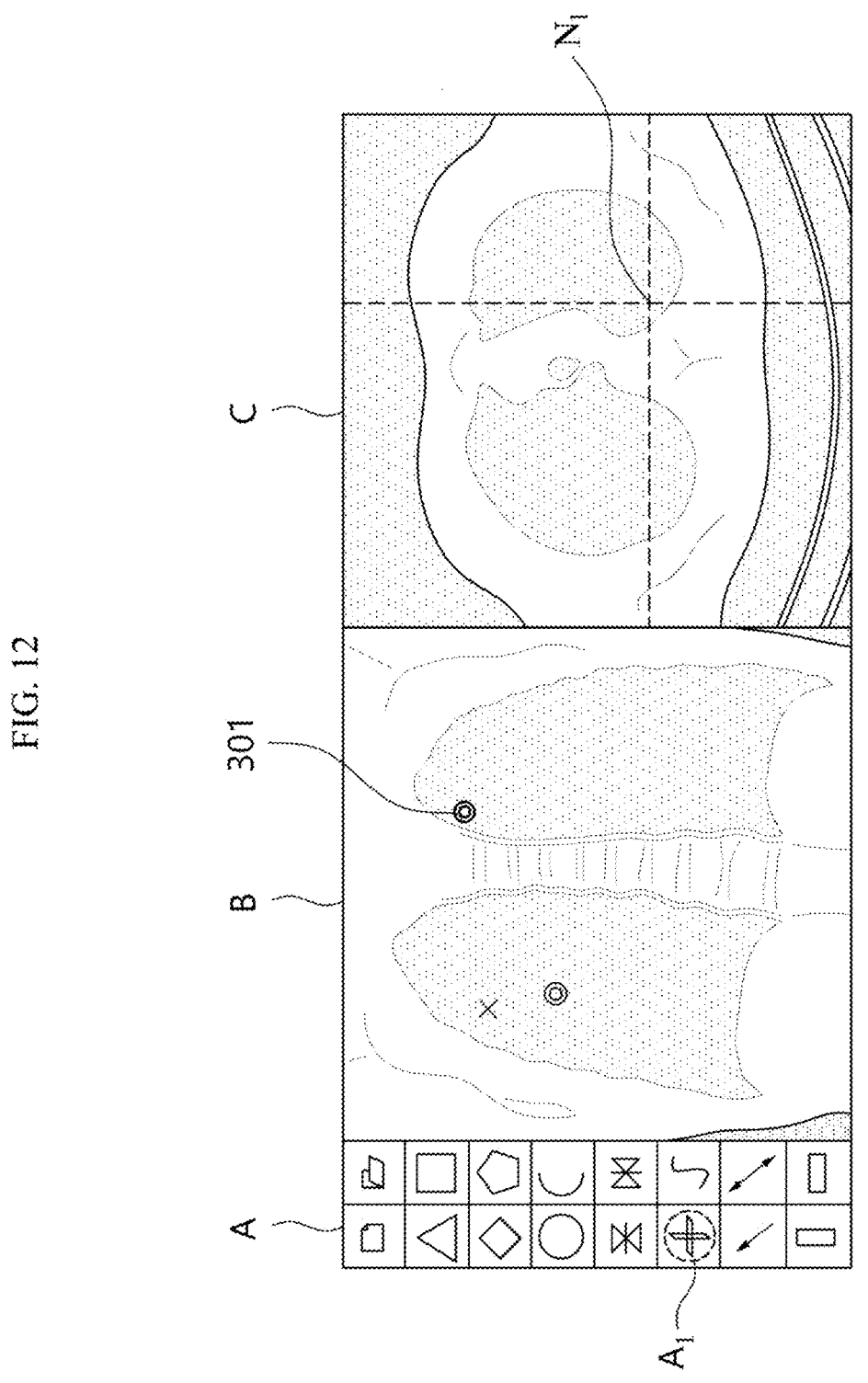

FIG. 12 is a diagram for explaining a method of utilizing a scout image according to the present invention. FIG. 12 schematically illustrates an execution screen of software for confirming dicom type medical image information using PACS.

Referring to FIG. 12, a tool area A may be displayed on one side of the screen, a scout image area B may be displayed in the center of the screen, and a medical image area C may be displayed on the other side of the screen. Although the screen configuration has been configured in three divisions for convenience of explanation, the screen configuration may be variously modified. For example, at least a portion of the tool area A, the scout image area B, and the medical image area C may be changed, or at least a portion of the three areas A, B, and C may be further divided to display additional information or images.

When the software executes the readout information including the scout image and the like, as shown in FIG. 12, the scout image area B displays the marking 301 at the location of the lesion.

When the marking 301 or the lesion is clicked using the 3D cursor A1 among the tools of the software for confirming dicom type medical image information, the medical image area C displays the corresponding lesion. The medical image is an original medical image included in the medical image information 100, and may be an image without marking and the like.

The software allows the corresponding medical image to be displayed in the medical image area C using the coordinates clicked by the 3D cursor.

However, as shown in FIG. 12, when the scout image is a coronal image, even if the marking 301 or the lesion is clicked using the 3D cursor A1, the x coordinate and z coordinate of the marking 301 or the lesion can be specified, but the y coordinate cannot be specified.

Thus, even if the marking 301 or the lesion is clicked using the 3D cursor A1 in the scout image of the read information that does not perform S32 and S33, the axial medical image image to be displayed in the medical image image area C can be specified using the clicked x coordinate and z coordinate, but the position of the lesion N1 in the axial medical image image cannot be specified. Therefore, the user needs to find the position of the lesion N1 in the axial medical image image again.

However, in the case of the read information indicating the Image Position Patient information (Xreal, Yreal, w) in the DICOM header information by S32 and S33, the axial medical image image to be displayed in the medical image image area C can be specified using the 3D cursor A1 in the scout image and the x coordinate and z coordinate and the Image Position Patient information (Xreal, Yreal, w), and the position of the lesion N1 in the axial medical image image can be specified (Xclick, Yreal, Zclick) or (Xreal, Yreal, Zclick). The Xclick means the x coordinate clicked using the 3D cursor A1, and the Zclick means the x coordinate clicked using the 3D cursor A1.

Referring to FIG. 12, in the medical image image area C, a vertical line corresponding to the Xclick or Xreal value and a horizontal line corresponding to the Yreal value can be displayed, and the intersection point between the vertical line and the horizontal line is the position of the lesion N1, so the user can easily identify the lesion N1 in the medical image image.

Alternatively, in the medical image image area C, only one of the vertical line corresponding to the Xclick or Xreal value and the horizontal line corresponding to the Yreal value can be displayed. In this case, the user can find the lesion n1 on the vertical line or the horizontal line in the medical image image, so the lesion N1 can be easily identified in the medical image image more easily.

Alternatively, in the case of the read information indicating the Image Position Patient information (u, Yreal, w) in the DICOM header information by S32 and S33, the axial medical image image to be displayed in the medical image image area C can be specified using the 3D cursor A1 in the scout image and the x coordinate and z coordinate and the Image Position Patient information (u, Yreal, w), and the position of the lesion in the axial medical image image image can be specified (Xclick, Yreal, Zclick).

One of ordinary skill in the art to which the present invention pertains can understand that the present invention can be implemented in other specific forms without changing its technical spirit or essential features. Therefore, the embodiments described above are to be illustrative in all aspects and not to be limiting. The scope of the present invention is represented by the claims to be described below rather than the detailed description, and all changes or modified forms derived from the meaning and scope of the claims and the equivalent concepts thereof should be interpreted as being included in the scope of the present invention.

The invention claimed is:

1. A medical image analysis support system, wherein the medical image analysis support system is configured to:

estimate, based on an artificial intelligence model trained to read lesions, a presence of a lesion from a plurality of medical images by reading medical image information including the plurality of medical images captured of a patient's body;

determine, based on the artificial intelligence model, a nodule type of the estimated lesion as at least one of a non-solid nodule, a part-solid nodule, a solid nodule, a calcified nodule, or unclassified;

detect a position and information of the estimated lesion; and generate readout information displaying markings related to the lesion on a scout image including at least one of the medical images in which the lesion is present and the medical images generated based on the plurality of medical images to represent the lesion, wherein the markings are displayed on the scout image corresponding to the position of the lesion and are displayed in different diagrams classified according to the nodule type of the lesion.

2. The medical image analysis support system according to claim 1, wherein a size of the diagram is displayed to correspond to the size of the lesion.

3. The medical image analysis support system according to claim 1, wherein the diagram is displayed in a dotted line, a solid line, or a double solid line according to the nodule type of the lesion.

4. The medical image analysis support system according to claim 1, wherein the medical image information and the readout information include data in DICOM (Digital Imaging and Communications in Medicine) format, wherein the medical image analysis support system is configured to determine coordinate information of an image position patient in DICOM header information of the readout information based on a coordinate information of the image position patient in DICOM header information of the medical images in which the lesion is present and a position information of the lesion in the medical images in which the lesion is present.

5. The medical image analysis support system according to claim 4, wherein the medical image analysis support system is configured to determine the position information of the lesion based on pixel spacing information in the DICOM header information of the medical images in which the lesion is present, and a number of pixels between a reference point corresponding to the coordinate information of the image position patient and the lesion.

6. A method of providing medical images analysis result, comprising:

estimating, based on an artificial intelligence model trained to read lesions, a presence of a lesion from a plurality of medical images by reading medical image information including the plurality of medical images captured of a patient's body, and detecting a position and information of the estimated lesion;

determining, based on the artificial intelligence model, a nodule type of the lesion as at least one of a non-solid nodule, a part-solid nodule, a solid nodule, a calcified nodule, or unclassified; and generating readout information displaying markings related to the lesion on a scout image including at least one of the medical images in which the lesion is present and the medical images generated based on the plurality of medical images to represent the lesion, wherein the markings are displayed on the scout image corresponding to the position of the lesion and are displayed in different diagrams classified according to the nodule type of the lesion.

7. The method of providing the medical images analysis result according to claim 6, wherein a size of the diagram is displayed to correspond to a size of the lesion.

8. The method of providing the medical images analysis result according to claim 6, wherein the diagram is displayed in a dotted line, a solid line, or a double solid line according to the nodule type of the lesion.

9. The method of providing the medical images analysis result according to claim 6, further comprising:

determining coordinate information of an image position patient in DICOM header information of the readout information based on coordinate information of the image position patient in DICOM header information of the medical images in which the lesion is present and position information of the lesion in the medical images in which the lesion is present.

10. The method of providing the medical images analysis result according to claim 9, further comprising:

determining the position information of the lesion based on pixel spacing information in the DICOM header information of the medical images in which the lesion is present, and a number of pixels between a reference point corresponding to the coordinate information of the image position patient and the lesion.

11. The medical image analysis support system according to claim 4, wherein the medical image analysis support system is configured to:

calculate three-dimensional coordinate information of the lesion using the position information of the lesion, and determine the calculated three-dimensional coordinate information as an image position patient value in the DICOM header information of the scout image;

obtain a user selection of one of the markings displayed on the scout image; and cause a medical image in which the lesion is located to be displayed based on the determined image position patient value.

* * * * *